(12) United States Patent
Falling et al.

(10) Patent No.: US 6,353,140 B1
(45) Date of Patent: Mar. 5, 2002

(54) PROCESS FOR THE PURIFICATION OF CYCLOPROPANECARBOXALDEHYDE

(75) Inventors: Stephen Neal Falling, Kingsport; Shannon Eugene Large, Blountville; Robert Joseph Maleski, Kingsport, all of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/877,860

(22) Filed: Jun. 8, 2001

Related U.S. Application Data

(60) Provisional application No. 60/241,816, filed on Oct. 19, 2000.

(51) Int. Cl.$^7$ ................................................ C07C 47/00
(52) U.S. Cl. ........................ 568/420; 568/426; 568/492
(58) Field of Search ................................. 568/420, 443, 568/448, 449, 450, 426, 492

(56) References Cited

U.S. PATENT DOCUMENTS

| | | | |
|---|---|---|---|
| 4,275,238 A | 6/1981 | Petree et al. | |
| 4,897,498 A | 1/1990 | Monnier et al. | |
| 4,950,773 A | 8/1990 | Monnier et al. | |
| 5,082,956 A | 1/1992 | Monnier et al. | |
| 5,254,701 A | 10/1993 | Falling et al. | |
| 5,315,019 A | 5/1994 | Phillips et al. | |
| 5,471,003 A * | 11/1995 | Liang | ........................ 568/420 |
| 5,502,257 A | 3/1996 | Liang et al. | |
| 5,536,851 A | 7/1996 | Monnier | |
| 5,955,627 A | 9/1999 | Nakazawa et al. | |
| 6,049,019 A | 4/2000 | Fortunak et al. | |
| 6,072,094 A | 6/2000 | Karady et al. | |
| 6,103,943 A * | 8/2000 | McCombs | ................... 568/908 |

FOREIGN PATENT DOCUMENTS

| | | |
|---|---|---|
| EP | 237956 | 1/1990 |
| EP | 430847 | 6/1991 |

OTHER PUBLICATIONS

Wang et al, J. Org. Chem. 2000, vol. 65, No. 6, pp. 1889–1891.
Wilson, J. Amer. Chem. Soc., 1947, vol. 69, pp. 3002–3004.
Smith at al, J. Amer. Chem. Soc., 1951, vol. 73, pp. 3831–3835.

* cited by examiner

Primary Examiner—Sreeni Padmanabhan
(74) Attorney, Agent, or Firm—Michael J. Blake; Bernard J. Graves

(57) ABSTRACT

Disclosed is process for the treatment of cyclopropanecarboxaldehdye (CPCA) which contains crotonaldehyde impurity with a base at elevated temperature to convert the crotonaldehyde to one or more higher boiling compounds followed by distillation to recover CPCA substantially free of crotonaldehyde. This selective reaction may be combined with a distillation to purify CPCA or in combination with the reaction of the CPCA in the treated mixture to produce a CPCA-derivative while avoiding or minimizing the formation of the analogous crotonaldehyde derivative.

16 Claims, No Drawings

PROCESS FOR THE PURIFICATION OF CYCLOPROPANECARBOXALDEHYDE

CROSS REFERENCE TO RELATED APPLICATION

This application claims the benefit of United States Provisional Application Serial No. 60/241,816 filed Oct. 19, 2000.

FIELD OF THE INVENTION

This invention pertains to a process for the purification of cyclopropanecarboxaldehdye (CPCA) which contains crotonaldehyde impurity by chemical treatment. More specifically, this invention pertains to a CPCA purification process wherein CPCA containing crotonaldehyde impurity is treated with a base at elevated temperature to convert the crotonaldehyde to one or more higher boiling compounds. CPCA substantially free of crotonaldehyde may be recovered by distillation. Alternatively, CPCA containing crotonaldehyde impurity may be treated with a base at elevated temperature to convert the crotonaldehyde to one or more higher boiling compounds followed by conversion of the CPCA to another compound which subsequently is separated from the higher boiling compounds.

BACKGROUND OF THE INVENTION

CPCA, 2,5-dihydrofuran (2,5-DHF), and 2,3-dihydrofuran (2,3-DHF) are important synthetic building blocks for organic chemical synthesis. CPCA is useful for introduction of the cyclopropane group into chemical compounds useful as human and veterinary drugs and pesticides. See, for example, U.S. Pat. No. 4,275,238, and European Patent Publications EP 237,955 A2, and EP 430,847 A1. CPCA is especially useful in the synthesis of cyclopropylacetylene which is an essential reagent in the synthesis of (S)-6-chloro-4-cyclopropylethynyl-4-trifluoromethyl-1,4-dihydro-2H-3,1-benzoxazin-2-one, a useful human immunodeficiency virus (HIV) reverse transcriptase inhibitor [U.S. Pat. Nos. 5,955,627, 6,049,019, and 6,072,094; Wang, et al., *J. Org. Chem.*, 65, 1889 (2000)]. 2,3-DHF is useful in the production of CPCA and for protection of alcohols and carboxylic acids [e.g., WO 99/00377; Mattson and Rapoport, *J. Org. Chem.*, 61, 6071 (1996)]. 2,5-DHF is useful for the production of 2,3-DHF and tetrahydrofuran (e.g., U.S. Pat. No. 4,962,210).

CPCA is derived from 1,3-butadiene by a sequence of four reactions. Monoepoxidation of 1,3-butadiene produces 3,4-epoxy-1-butene (EPB) as described in U.S. Pat. Nos. 4,897,498 and 4,950,773. This epoxide is isomerized to 2,5-DHF (U.S. Pat. Nos. 5,082,956 and 5,315,019) which is isomerized to 2,3-DHF (U.S. Pat. Nos. 5,254,701 and 5,536,851). Finally, 2,3-DHF is isomerized to CPCA (C. L. Wilson, *J. Amer. Chem. Soc.*, 69, 3002 (1947) and U.S. Pat. No. 5,502,257).

Production of CPCA, 2,5-DHF, and 2,3-DHF often results in the co-production of low levels of the unwanted side-product crotonaldehyde ($CH_3CH=CHCHO$). This material is isomeric with EPB, 2,5-DHF, 2,3-DHF and CPCA. For some purposes the mixture of crotonaldehyde with CPCA, 2,5-DHF or 2,3-DHF can be used in the next process step. However, it is often necessary to produce CPCA essentially free of crotonaldehyde. In mixtures with 2,5-DHF (bp 66° C.) and/or 2,3-DHF (bp 55° C.), crotonaldehyde (bp 104° C.) can be removed by fractional distillation due to its significantly higher boiling point. However, CPCA (bp 100° C.) is virtually impossible to separate from crotonaldehyde by fractional distillation due to its similar boiling point. As aldehydes, CPCA and crotonaldehyde have similar chemical reactivities thereby reducing the possibilities for using CPCA/crotonaldehyde mixtures in the production of CPCA derivatives. Purification of CPCA, therefore, presents an especially important and difficult problem.

U.S. Pat. No. 5,471,003 describes a process for the purification of CPCA contaminated with crotonaldehyde by the selective hydrogenation of the crotonaldehyde to butyraldehyde followed by distillation to separate the butyraldehyde from the cyclopropanecarboxaldehyde. However this distillation is difficult, especially when water is present in the mixture. For these reasons there is a need for an effective and easily practiced process to remove crotonaldehyde from CPCA.

McCombs, U.S. Pat. No. 6,103,943 describes a process for the production of 3-buten-1-ol by the reduction of 3,4-epoxy-1-butene. The process also produces crotonaldehyde as an impurity. The conversion of crotonaldehyde in the mixture to a high-boiling imine with a stoichiometric amount of a primary or secondary amine permits isolation of pure 3-buten-1-ol by distillation. The McCombs patent also mentions the conversion of crotonaldehyde to its dimer by the addition of an alkali metal hydroxide or carbonate to the crude 3-buten-1-ol product mixture.

SUMMARY OF THE INVENTION

It has been discovered that crotonaldehyde present as an impurity in CPCA reacts selectively upon treatment with base to form higher boiling materials or derivatives. The present invention, therefore, provides a process which comprises contacting a mixture comprising CPCA and crotonaldehyde with a base selected from secondary amines, alkali metal hydroxides, alkali metal carbonates, alkaline earth hydroxides, alkaline earth carbonates and basic ion exchange resins at elevated temperature whereby crotonaldehyde is converted to high boiling materials or derivatives, i.e., derivatives having a boiling point significantly above the boiling point of CPCA, provided that the CPCA remains substantially unconverted. That is, the base converts the crotonaldehyde to high boilers preferentially to the CPCA. For example, less than about 15% of the CPCA is converted to other materials; preferably, less than about 10% and more preferably less than about 5% of the CPCA is converted. The present invention includes an economical and effective means for the purification of CPCA contaminated with crotonaldehyde by the selective conversion of the crotonaldehyde to one or more higher boiling materials followed by distillation. This second embodiment concerns a process for the purification of CPCA containing crotonaldehyde impurity which comprises the steps of:

(1) contacting a mixture comprising CPCA and crotonaldehyde with a base selected from secondary amines, alkali metal hydroxides, alkali metal carbonates, alkaline earth hydroxides, alkaline earth carbonates and basic ion exchange resins at elevated temperature; and (2) distilling the mixture resulting from step (1) to recover CPCA substantially free of crotonaldehyde as a distillate. In the process for the purification of CPCA containing crotonaldehyde as an impurity, all, or essentially all, of the crotonaldehyde reacts selectively with itself to form crotonaldehyde derivatives having boiling points significantly higher than the boiling point of CPCA. Thus, CPCA can be separated readily from the crotonaldehyde derivatives to recover CPCA substantially free of crotonaldehyde.

In another embodiment of the present invention, a mixture comprising CPCA and crotonaldehyde is treated with a base at elevated temperature to convert the crotonaldehyde to high boiling materials or derivatives, then converting the CPCA to a CPCA-derivative, i.e., another compound derived directly or indirectly from CPCA, and distilling or crystallizing a mixture of the CPCA-derivative and high boiling crotonaldehyde derivatives to recover the CPCA-derivative substantially free of crotonaldehyde as a distillate or solid. This third embodiment of the invention is directed to a process for the preparation and recovery of a CPCA-derivative wherein CPCA containing crotonaldehyde impurity is used as a reactant which comprises the steps of:

(i) contacting a mixture comprising CPCA and crotonaldehyde with a base selected from secondary amines, alkali metal hydroxides, alkali metal carbonates, alkaline earth hydroxides, alkaline earth carbonates and basic ion exchange resins at elevated temperature whereby crotonaldehyde is converted to one or more high boiling derivatives, provided that the CPCA remains substantially unconverted; and (ii) reacting the CPCA-containing mixture of step (i) with a reactant which reacts with CPCA to form a CPCA derivative but does not react, or does not react significantly, with the high boiling crotonaldehyde derivatives of step (i).

The CPCA derivative produced in step (ii) may be separated from the high boiling crotonaldehyde derivative by distillation or crystallization. The reaction contemplated by step (ii) normally would include the reaction of crotonaldehyde. However, the crotonaldehyde derivatives selectively produced in step (i) are inert with respect to the reaction of step (ii). Thus, all, or essentially all, of the crotonaldehyde is not available for reaction in step (ii).

The mechanism of conversion of crotonaldehyde to one or more materials having boiling points significantly higher than the boiling point (100° C.) of CPCA is believed to be due to aldol condensations, enamine alkylations and conjugate additions. The process of the invention involves the selective reaction of crotonaldehyde while the other aldehyde present in the mixture, CPCA, remains substantially unreacted or unconverted.

DETAILS OF THE INVENTION

The impure CPCA used in the process may contain up to about 50 weight percent, e.g., about 1 to 50 weight percent, crotonaldehyde, more typically about 1 to 20 weight percent crotonaldehyde, based on the total weight of the CPCA and crotonaldehyde. Other impurities which may be present in the CPCA include 2,5-DHF, 2,3-DHF, tetrahydrofuran, water, and cyclopropanecarboxylic acid which also are separated from the CPCA by the distillation in the second step of the process of our invention. Although water also boils at 100° C., a minimum boiling azeotrope with CPCA (bp 68° C.) is easily removed first during the distillation. For some uses of CPCA, complete removal of water is unnecessary.

Examples of bases useful in the present invention include secondary amines such as dialkylamines, di(hydroxyalkyl) amines, dicycloalkylamines and cyclic amines containing up to about 40 carbon atoms, preferably about 4 to 20 carbon atoms. Examples of the alkali and alkaline earth metal hydroxides and carbonates include the hydroxides and carbonates of potassium, sodium, lithium, cesium, magnesium, calcium and barium. The preferred basic catalysts are secondary amines, e.g., amines having the formula $(R)_2NH$ wherein each R is independently selected from alkyl containing from about 1 to 20, preferably about 2 to 10 carbon atoms, hydroxyalkyl containing 2 to about 4 carbon atoms, and cycloalkyl such as cyclohexyl or the two R groups collectively may represent a group which, with the nitrogen to which they are attached, forms a cyclic amine, e.g. morpholine, piperidine and pyrrolidine. Particularly preferred secondary amines are dicyclohexylamine, bis(2-ethylhexyl)amine, and diethanolamine. Primary amines are not useful for removal of crotonaldehyde from CPCA because they are non-selective and destroy a large fraction of CPCA. Although useful, the inorganic bases such as alkali metal or alkaline earth hydroxides and carbonates are not preferred due to poor solubility or the need to include water in the process. Most preferred among the inorganic bases is sodium hydroxide. Basic resins include strongly basic ion exchange resins (hydroxide form) and resins with secondary amine functionality.

The amount of base used may vary significantly from a catalytic amount to a stoichiometric excess based on the amount of crotonaldehyde present, e.g., from about 0.05 to 2 moles of base per mole of crotonaldehyde. The amount of base used preferably is a catalytic amount, e.g., about 0.05 to 0.5 moles base per mole of crotonaldehyde. The successful use of a catalytic amount of base is in contrast to the teaching of McCombs and indicates that the crotonaldehyde is not merely converted to a high-boiling imine but rather is converted into higher-boiling oligomeric or polymeric materials. Although the base may be used in stoichiometric or greater amounts, the catalytic nature of this crotonaldehyde conversion results in a lower cost process with fewer high-boilers for disposal. When the base is diethanolamine, only a catalytic amount should be used due to side production of the cyclic aminal of CPCA. Generation of this aminal results in loss of CPCA and represents a potential hazard due to a high release of energy upon decomposition at elevated temperatures.

The first step of the process of the present invention is carried out at elevated temperature for a period of time sufficient to convert all, or essentially all, of the crotonaldehyde to one or more higher boiling materials. The time required to convert the crotonaldehyde depends on its concentration, the amount and choice of basic catalyst, and temperature. Typical conditions for the crotonaldehyde removal are a reaction time of 2 to 48 hours at 50 to 120° C., or more typically 15 to 24 hours at 80 to 100° C. Pressure is not an important factor in the operation of the first step of our novel process and, therefore, pressures moderately above or below ambient pressure may be used. The process preferably is operated at the atmospheric pressure boiling point of the mixture.

The first step of the process of this invention may be carried out in the absence or in the presence of an inert solvent or diluent. Examples of permissible solvents include aliphatic, cycloaliphatic and aromatic hydrocarbons such as cyclohexane, heptane, toluene, xylene and mixed xylene isomers, ethers such as tetrahydrofuran, alcohols such as methanol, ethanol and n-butanol. Preferably the process of this invention is carried out using the impure CPCA containing crotonaldehyde without the use of an inert solvent or diluent.

The second step of the second embodiment utilizes a conventional distillation for the recovery of CPCA free, or essentially free, of crotonaldehyde. The amount of crotonaldehyde in the distilled CPCA may be up to about 0.2 weight percent based on the weight of the CPCA distilled. However, the amount of crotonaldehyde present preferably ranges from no detectable crotonaldehyde up to about 0.1 weight percent. The pressure of the second step can be adjusted as necessary for batch or continuous distillation. Pressures moderately above or below ambient pressure may be used. The distillation preferably is operated at ambient pressure.

The distillation normally is operated as a batch process after the first step is completed. However, the process of the second embodiment may be carried out in a continuous manner wherein both of the steps are performed concurrently or simultaneously. For example, the basic catalyst, e.g., a secondary amine having a boiling point greater than about 120° C., may be fed to the mid- or upper section and CPCA containing crotonaldehyde may be fed to the mid- or lower section of a reactive distillation column. Alternatively, the CPCA containing crotonaldehyde and the secondary amine may be mixed and then fed to the reactive distillation column. The CPCA and other low boilers are distilled from the top or upper part of the column. The crotonaldehyde is converted in the column into high-boiling materials which are intermittently or continuously purged from the base of the column along with basic catalyst. A second distillation may be required to separate CPCA from low boilers.

The process described herein may be used to assist in the separation of crotonaldehyde present as an impurity in other chemicals such as tetrahydrofuran, 2,5-DHF, and 2,3-DHF. However, as mentioned above, crotonaldehyde can be removed from these materials by fractional distillation due to its significantly higher boiling point.

The reaction of step (ii) of the third embodiment of the present invention may be any reaction wherein an aldehyde is converted to another compound through the reactivity of the aldehyde group. Examples of such reactions include reactions of CPCA with primary amines such as alkylamines to produce N-cyclopropylmethyl-N-alkylamines, and the reaction of CPCA with malonic acid to form 3-cyclopropylpropenoic acid.

EXAMPLES

The process of the present invention is further illustrated by the following examples. Analytical results were determined by conventional gas chromatography (GC) procedures.

Example 1

To a 100-mL, three-neck, round-bottom flask was added 50.0 g of 90.0% CPCA (7.9% crotonaldehyde (4.0 g, 0.057 mole)) and 1 mL (0.005 mole) of dicyclohexylamine. The flask was equipped with a heating mantle, condenser, thermocouple, and magnetic stirrer. The mixture was heated under a nitrogen atmosphere to reflux (95–96° C.) and sampled periodically for analysis. After 3 hours, GC analysis showed only 0.68% crotonaldehyde. After 18 hours the mixture was distilled to give a product fraction at 96° C. (35.3 g). GC analysis of the distillate showed 99.1% CPCA and 0.11% crotonaldehyde. The recovery of available CPCA was 77.7%.

Example 2

To a 100-mL, three-neck, round-bottom flask was added 50.0 g of 90% CPCA (7.9% crotonaldehyde (4.0 g, 0.057 mole)) and 0.6 g (0.006 mole) of diethanolamine. The flask was equipped with a heating mantle, distillation head, thermocouple, and magnetic stirrer. The mixture was heated under a nitrogen atmosphere to reflux (96–100° C.) and sampled periodically for analysis. After 22 hours, GC analysis showed no crotonaldehyde. The mixture was distilled to give a product fraction at 98–100° C. GC analysis of the distillate showed only CPCA and no crotonaldehyde.

Example 3

To a 250-mL, three-neck, round-bottom flask was added 175.0 g of 85.7% CPCA (7.1% crotonaldehyde) and 1.41 g (0.00584 mole) of bis(2-ethylhexyl)amine. The flask was equipped with a heating mantle, condenser, thermocouple, and magnetic stirrer. The mixture was heated under a nitrogen atmosphere to reflux (95° C.) and sampled periodically for analysis. After 37 hours the mixture was distilled to give 140.9 g of distillate. GC analysis of the distillate showed 94.1% CPCA and 0.22% crotonaldehyde. The pot residue (21.7 g) showed 8.39% CPCA and 0.07% crotonaldehyde. The recovery of CPCA was 88.5%.

Example 4

To a 1000-mL, three-neck, round-bottom flask was added 600.0 g of 92% CPCA (6.2% crotonaldehyde (37.2 g, 0.531 mole)) and 22 g (0.21 mole) of diethanolamine. The flask was equipped with a heating mantle, distillation head, thermocouple, and magnetic stirrer. The mixture was heated under a nitrogen atmosphere to reflux (96–100° C.) and held there for 12 hours. GC analysis showed 0.1% crotonaldehyde.

Example 5

A portion of the CPCA solution produced in Example 4 was converted to 3-cyclopropylpropenoic acid by the reaction of CPCA with malonic acid using an adaptation of a standard method [J. Amer. Chem. Soc., 73, 3831, 3835 (1951)]. GC analysis of the crude product, on a solvent free basis, showed 91.9% 3-cyclopropylpropenoic acid and <0.1% sorbic acid (derived from the small amount of crotonaldehyde in the CPCA reactant used). When this reaction is carried out using the untreated CPCA described in Example 4, the crude product contains 83.3% 3-cyclopropylpropenoic acid and 3.1% sorbic acid.

Example 6

A portion of the CPCA solution produced in Example 4 was converted to N-cyclopropylmethyl-N-n-propylamine by the reaction of CPCA with n-propylamine under reductive conditions according to the procedure described in U.S. Pat. No. 4,275,238. After distillation, GC analysis showed 99.6% N-cyclopropylmethyl-N-n-propylamine and <0.1% of N-n-butyl-N-n-propyl amine (derived from the small amount of crotonaldehyde in the starting CPCA). When this reaction is carried out using the untreated CPCA described in Example 4, the product contains 99.1% N-cyclopropylmethyl-N-n-propylamine and 0.7% of the N-n-butyl-N-n-propyl amine.

The invention has been described in detail with particular reference to preferred embodiments thereof, but it will be understood that variations and modifications can be effected within the spirit and scope of the invention.

We claim:

1. Process which comprises contacting a mixture comprising cyclopropanecarboxaldehyde (CPCA) and crotonaldehyde with a base selected from secondary amines, alkali metal hydroxides, alkali metal carbonates, alkaline earth hydroxides, alkaline earth carbonates and basic ion exchange resins at elevated temperature whereby crotonaldehyde is converted to one or more high boiling derivatives, provided that the CPCA remains substantially unconverted.

2. Process according to claim 1 wherein CPCA containing about 1 to 50 weight percent crotonaldehyde, based on the total weight of the CPCA and crotonaldehyde is heated at a temperature of about 50 to 120° C.

3. Process according to claim 1 wherein CPCA containing about 1 to 20 weight percent crotonaldehyde, based on the total weight of the CPCA and crotonaldehyde and about 0.05 to 2 moles per mole of crotonaldehyde of a secondary amine containing 4 to 20 carbon atoms is heated at a temperature of about 80 to 100° C.

4. Process which comprises heating a mixture comprising cyclopropanecarboxaldehyde (CPCA) and about 1 to 50 weight percent crotonaldehyde, based on the total weight of the CPCA and crotonaldehyde, at a temperature of about 50 to 120° C. in the presence of a secondary amine having the formula $(R)_2NH$ wherein each R is independently selected from alkyl containing from about 2 to 10, hydroxyalkyl containing 2 to about 4 carbon atoms, and cyclohexyl or the formula $(R)_2NH$ may represent morpholine, piperidine or pyrrolidine; and the amount of secondary amine present is about 0.05 to 2 moles per mole of crotonaldehyde.

5. Process according to claim 4 wherein CPCA containing about 1 to 20 weight percent crotonaldehyde, based on the total weight of the CPCA and crotonaldehyde, is heated at a temperature of about 80 to 100° C. in the presence of a secondary amine selected from dicyclohexylamine, bis(2-ethylhexyl)amine, and diethanolamine.

6. Process for the purification of cyclopropanecarboxaldehyde (CPCA) containing crotonaldehyde impurity which comprises the steps of:
   (1) contacting a mixture comprising CPCA and crotonaldehyde with a base selected from secondary amines, alkali metal hydroxides, alkali metal carbonates, alkaline earth hydroxides, alkaline earth carbonates and basic ion exchange resins at elevated temperature; and
   (2) distilling the mixture resulting from step (1) to recover CPCA substantially free of crotonaldehyde as a distillate.

7. Process according to claim 6 wherein step (1) comprises heating CPCA containing about 1 to 50 weight percent crotonaldehyde, based on the total weight of the CPCA and crotonaldehyde at a temperature of about 50 to 120° C. and the CPCA recovered from the distillation of step (2) contains 0.2 or less weight percent crotonaldehyde.

8. Process according to claim 6 wherein step (1) comprises heating CPCA containing about 1 to 20 weight percent crotonaldehyde, based on the total weight of the CPCA and crotonaldehyde and about 0.05 to 2 moles per mole of crotonaldehyde of a secondary amine containing 4 to 20 carbon atoms at a temperature of about 80 to 100° C. and the CPCA recovered from the distillation of step (2) contains 0.2 or less weight percent crotonaldehyde.

9. Process for the purification of cyclopropanecarboxaldehyde (CPCA) containing crotonaldehyde impurity which comprises the steps of:
   (1) heating CPCA containing about 1 to 50 weight percent crotonaldehyde, based on the total weight of the CPCA and crotonaldehyde, at a temperature of about 50 to 120° C. in the presence of a secondary amine having the formula $(R)_2NH$; and
   (2) distilling the mixture resulting from step (1) to recover CPCA substantially free of crotonaldehyde as a distillate;
wherein each R is independently selected from alkyl containing from about 2 to 10, hydroxyalkyl containing 2 to about 4 carbon atoms, and cyclohexyl or the formula $(R)_2NH$ may represent morpholine, piperidine or pyrrolidine; and the amount of secondary amine present is about 0.05 to 2 moles per mole of crotonaldehyde.

10. Process according to claim 9 wherein step (1) comprises heating CPCA containing about 1 to 20 weight percent crotonaldehyde, based on the total weight of the CPCA and crotonaldehyde, at a temperature of about 80 to 100° C. in the presence of a secondary amine selected from dicyclohexylamine, bis(2-ethylhexyl)amine, and diethanolamine; and the CPCA recovered from the distillation of step (2) contains 0.2 or less weight percent crotonaldehyde.

11. Process for the preparation of a derivative of cyclopropanecarboxaldehyde (CPCA) wherein CPCA containing crotonaldehyde impurity is used as a reactant which comprises the steps of:
   (i) contacting a mixture comprising CPCA and crotonaldehyde with a base selected from secondary amines, alkali metal hydroxides, alkali metal carbonates, alkaline earth hydroxides, alkaline earth carbonates and basic ion exchange resins at elevated temperature whereby crotonaldehyde is converted to one or more high boiling derivatives provided that the CPCA remains substantially unconverted; and
   (ii) reacting the CPCA-containing mixture of step (i) with a reactant which reacts with CPCA to form a CPCA derivative but does not react significantly with the high boiling crotonaldehyde derivatives of step (i).

12. Process according to claim 11 wherein step (i) comprises heating CPCA containing about 1 to 50 weight percent crotonaldehyde, based on the total weight of the CPCA and crotonaldehyde at a temperature of about 50 to 120° C. and the reactant employed in step (ii) is selected from primary amines and malonic acid.

13. Process according to claim 11 wherein step (i) comprises heating CPCA containing about 1 to 20 weight percent crotonaldehyde, based on the total weight of the CPCA and crotonaldehyde and about 0.05 to 2 moles per mole of crotonaldehyde of a secondary amine containing 4 to 20 carbon atoms at a temperature of about 80 to 100° C. and the reactant employed in step (ii) is selected from alkylamines and malonic acid.

14. Process for the preparation and recovery of a derivative of cyclopropanecarboxaldehyde (CPCA) selected from N-cyclopropylmethyl-N-alkylamines and 3-cyclopropylpropenoic acid wherein CPCA containing crotonaldehyde impurity is used as a reactant which comprises the steps of:
   (i) heating CPCA containing about 1 to 50 weight percent crotonaldehyde, based on the total weight of the CPCA and crotonaldehyde, at a temperature of about 50 to 120° C. in the presence of a secondary amine having the formula $(R)_2NH$;
   (ii) reacting the CPCA-containing mixture of step (i) with a reactant selected from N-alkylamines and malonic acid which reacts with CPCA to form the CPCA derivative but does not react with the high boiling crotonaldehyde derivatives of step (i); and
   (iii) distilling the mixture resulting from step (ii) to recover the CPCA-derivative;
wherein each R is independently selected from alkyl containing from about 2 to 10, hydroxyalkyl containing 2 to about 4 carbon atoms, and cyclohexyl or the formula $(R)_2NH$ may represent morpholine, piperidine or pyrrolidine; and the amount of secondary amine present is about 0.05 to 2 moles per mole of crotonaldehyde.

15. Process according to claim 14 wherein the derivative of cyclopropanecarboxaldehyde (CPCA) is an N-cyclopropylmethyl-N-alkylamine, step (i) comprises heating CPCA containing about 1 to 20 weight percent crotonaldehyde, based on the total weight of the CPCA and crotonaldehyde, at a temperature of about 80 to 100° C. in the presence of a secondary amine selected from dicyclohexylamine, bis(2-ethylhexyl)amine, and diethanolamine; and the reactant employed in step (ii) is an alkylamine.

16. Process according to claim 14 wherein the derivative of cyclopropanecarboxaldehyde (CPCA) is 3-cyclopropylpropenoic acid, step (i) comprises heating CPCA containing about 1 to 20 weight percent crotonaldehyde, based on the total weight of the CPCA and crotonaldehyde, at a temperature of about 80 to 100° C. in the presence of a secondary amine selected from dicyclohexylamine, bis(2-ethylhexyl)amine, and diethanolamine; and the reactant employed in step (ii) is malonic acid.

\* \* \* \* \*